United States Patent
Itoh

(10) Patent No.: US 9,028,755 B2
(45) Date of Patent: May 12, 2015

(54) SPECIMEN TRANSPORT APPARATUS, SPECIMEN PROCESSING APPARATUS, AND SPECIMEN TRANSPORT METHOD

(71) Applicant: Aoi Seiki, Co., Ltd., Kumamoto-shi, Kumamoto-ken (JP)

(72) Inventor: Teruaki Itoh, Kumamoto (JP)

(73) Assignee: Aoi Seiki Co., Ltd., Kumamoto-shi, Kumamoto-ken (JP)

( * ) Notice: Subject to any disclaimer, the term of this patent is extended or adjusted under 35 U.S.C. 154(b) by 0 days.

(21) Appl. No.: 14/028,758

(22) Filed: Sep. 17, 2013

(65) Prior Publication Data

US 2014/0086808 A1   Mar. 27, 2014

(30) Foreign Application Priority Data

Sep. 21, 2012 (JP) ................... 2012-208305
Nov. 21, 2012 (JP) ................... 2012-255720

(51) Int. Cl.
  *G01N 35/04* (2006.01)
  *B01L 9/00* (2006.01)
(52) U.S. Cl.
  CPC . *B01L 9/00* (2013.01); *G01N 35/04* (2013.01); *G01N 2035/0408* (2013.01); *G01N 2035/0429* (2013.01); *G01N 2035/0484* (2013.01)
(58) Field of Classification Search
  None
  See application file for complete search history.

(56) References Cited

U.S. PATENT DOCUMENTS

| | | | | |
|---|---|---|---|---|
| 3,187,182 A | * | 6/1965 | Fratantuno | 250/328 |
| 3,302,025 A | * | 1/1967 | Palic et al. | 250/328 |
| 3,722,790 A | * | 3/1973 | Natelson | 494/11 |
| 4,692,308 A | * | 9/1987 | Riley et al. | 422/65 |
| 4,795,023 A | | 1/1989 | Gibbemeyer | |
| 4,861,553 A | | 8/1989 | Mawhirt et al. | |
| 6,081,326 A | * | 6/2000 | Rousseau et al. | 356/246 |
| 6,202,829 B1 | | 3/2001 | van Dyke, Jr. et al. | |
| 6,358,471 B1 | * | 3/2002 | Ishihara | 422/65 |
| 2006/0286619 A1 | * | 12/2006 | Ricci et al. | 435/13 |
| 2007/0000352 A1 | * | 1/2007 | Itoh | 81/3.2 |
| 2008/0190735 A1 | * | 8/2008 | Luoma | 198/340 |
| 2008/0318306 A1 | * | 12/2008 | Le Comte et al. | 435/287.3 |
| 2009/0158863 A1 | * | 6/2009 | Shanafelter | 73/864.81 |
| 2009/0257916 A1 | * | 10/2009 | Itoh | 422/63 |
| 2009/0260457 A1 | * | 10/2009 | Itoh | 73/863.91 |
| 2011/0053169 A1 | * | 3/2011 | Macioszek et al. | 435/6 |

FOREIGN PATENT DOCUMENTS

| | | |
|---|---|---|
| CN | 1930479 | 3/2007 |
| EP | 0 549 573 A1 | 6/1993 |
| JP | 2000-162215 | 6/2000 |
| JP | 2011-13086 | 1/2011 |
| WO | WO 95/03548 | 2/1995 |

OTHER PUBLICATIONS

Search report in EP 13 00 4536 dated Dec. 18, 2013.
Chinese Office Action mailed Jul. 31, 2014 issued in Chinese Patent Application No. 201310426009.4, 16 pp.
Taiwanese Office Action dated Mar. 3, 2015 issued in Taiwan Patent Application No. 102133546 and English Translation, 9 pp.

* cited by examiner

*Primary Examiner* — Jill Warden
*Assistant Examiner* — Benjamin Whatley
(74) *Attorney, Agent, or Firm* — Nixon & Vanderhye P.C.

(57) ABSTRACT

A specimen transport apparatus according to an aspect is provided with a holder which holds a cup-like specimen container accommodating a specimen in an upright position, a chain member disposed along a predetermined transport path, and a supporting portion provided in a predetermined position on the chain member and configured to support the holder.

2 Claims, 5 Drawing Sheets

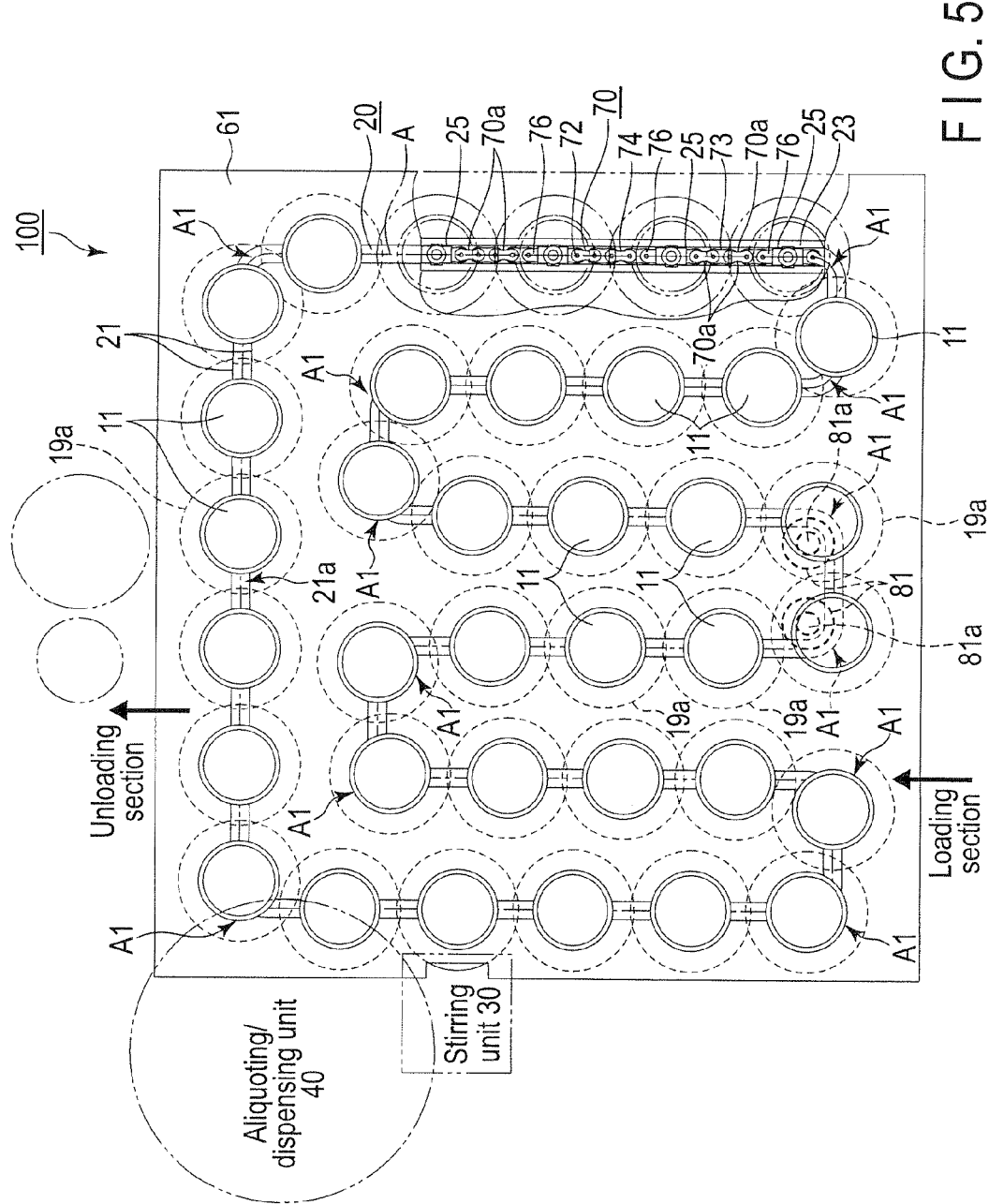

SPECIMEN TRANSPORT APPARATUS, SPECIMEN PROCESSING APPARATUS, AND SPECIMEN TRANSPORT METHOD

CROSS-REFERENCE TO RELATED APPLICATIONS

This application is based upon and claims the benefit of priority from the prior Japanese Patent Applications No. 2012-208305, filed Sep. 21, 2012; and No. 2012-255720, filed Nov. 21, 2012, the entire contents of which are incorporated herein by reference.

BACKGROUND OF THE INVENTION

1. Field of the Invention

The present invention relates to a specimen transport apparatus, specimen processing apparatus, and specimen transport method.

2. Description of the Related Art

In some tests, such as sediment, qualitative, and biochemical tests, specimens, e.g., urine samples accommodated in urine cups or other specimen containers, are transported along a predetermined path that passes through various processing stations. A belt conveyor system is a typical transport mechanism for urine cups, in which holders that engage with transport rails on either side are placed on a belt and transported by running the belt (Jpn. Pat. Appin. KOKAI Publication No. 2011-013086).

The transport of cup-like specimen containers requires an upright position to be maintained to prevent the containers from tilting or toppling over due to misalignment.

BRIEF SUMMARY OF THE INVENTION

A specimen transport apparatus according to an aspect comprises a holder which holds a cup-like specimen container accommodating a specimen in an upright position, a chain member disposed along a predetermined transport path, and a supporting portion provided in a predetermined position on the chain member and configured to support the holder.

A specimen processing apparatus according to another aspect comprises the specimen transport apparatus described above, a stirring unit located beside the transport path and configured to rotate the specimen container in an upright position, thereby stirring the specimen therein, and an aliquoting/dispensing unit located downstream relative to the stirring unit in the transport path and configured to distribute and dispense the specimen in the specimen container into another container.

A specimen transport method according to another aspect comprises holding a cup-like specimen container accommodating a specimen in an upright position by means of a holder and feed-driving a chain member disposed along a predetermined transport path in such a manner that the holder is supported in a predetermined position on the chain member.

According to an embodiment, the specimen container can be transported in an upright position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a plan view showing a specimen processing apparatus according to another embodiment.

DETAILED DESCRIPTION OF THE INVENTION

Figure 1:
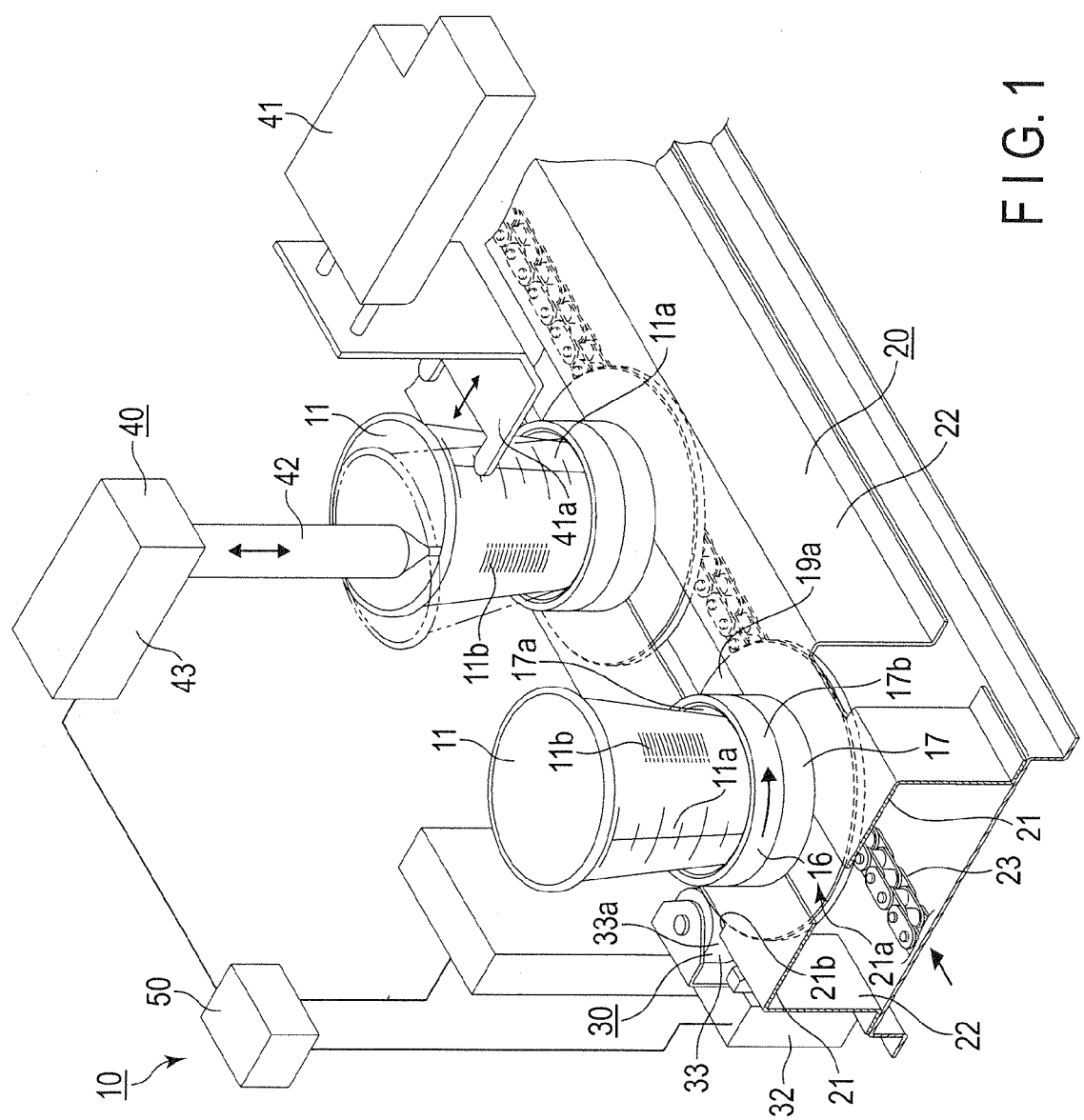
FIG. 1 is an explanatory diagram of a specimen processing apparatus according to a first embodiment of the invention.
Figure 2:
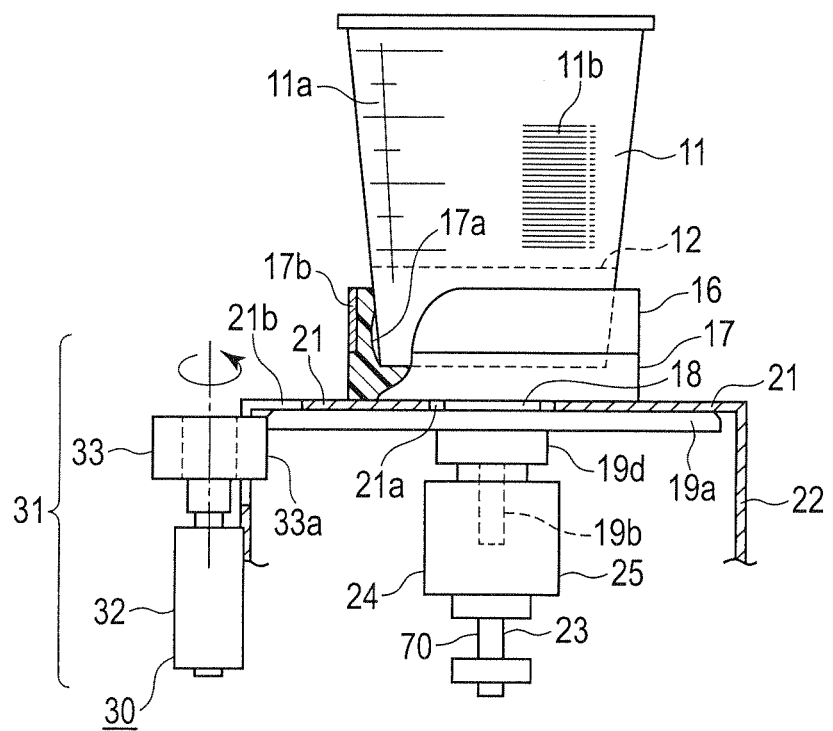
FIG. 2 is a cutaway side view of a stirring unit according to the embodiment.

A specimen processing apparatus 10 according to a first embodiment of the present invention will now be described with reference to FIGS. 1 and 2. FIG. 1 is an explanatory diagram of the specimen processing apparatus 10 of the present embodiment, and FIG. 2 is a cutaway side view of a stirring unit 30 and shows, partially in section, a frame 22 and the like. In each of these drawings, configurations are enlarged, reduced, or omitted as required for ease of explanation. In these drawings, arrows X, Y and Z individually indicate three orthogonal directions.

The specimen processing apparatus 10 is an apparatus that previously stirs, distributes, and dispenses a specimen prior to various inspection processes, and is used as, for example, a pre-treatment unit of an analyzer. The specimen processing apparatus 10 comprises a transport unit 20, the stirring unit (stirrer) 30, an aliquoting/dispensing unit 40, and a control unit 50. The transport unit 20 transports a cup 11 for use as a specimen container along a predetermined transport path. The stirring unit 30 is configured to rotate the transported cup 11 together with a holder 16, thereby stirring a specimen 12. The aliquoting/dispensing unit 40 distributes the specimen 12 from the cup 11 immediately after the stirring and dispenses it into a Spitz tube or the like. The control unit 50 controls the operations of the individual units. Further, various processing units are installed on the upstream and downstream sides of the transport path, whereby the transported cup 11 or the specimen therein is subjected to various steps of processing.

In the present embodiment, the specimen 12 is a urine sample and the cup 11 for use as the specimen container is cylindrical. For example, the cup 11 is an open-topped circular cylinder of paper having an internal space that accommodates the urine sample. The cup 11 is tapered from top to bottom and is supported and transported in an upright position with its lower part fitted in a holding portion 17 of the holder 16. Various specimen data, such as a scale 11a for gauging the amount of the specimen, barcode 11b representative of identification data on the specimen, etc., are displayed on the outer peripheral surface of the cup 11. In the present embodiment, the cup 11 has a bottom diameter of about 30 to 100 mm, top opening diameter of 50 to 150 mm, and height of 30 to 100 mm, for example.

As shown in FIGS. 1 and 2, the holder 16 integrally comprises the holding portion 17, neck portion 18, and large-diameter turntable 19, which are coaxial with one another. The holding portion 17 is configured to hold the outer surface of the lower part of the cup 11. The neck portion 18 is located continuously with the bottom of the holding portion 17. The turntable 19 adjoins the bottom of the neck portion 18.

The holding portion 17 is a bottomed circular cylinder the top side of which is expanded in diameter. The holding portion 17 comprises a cylindrical portion 17a and metallic outer layer 17b. The cylindrical portion 17a is a bottomed circular cylinder of resin. The outer layer 17b covers a part of the outer periphery of the cylindrical portion 17a. The cup 11 can be held in a substantially vertical upright position in a circular accommodation space, with the inner surface of the resin cylindrical portion 17a in close contact with the outer periphery of the cup 11.

The neck portion 18 is integrally molded so that it adjoins the bottom of the holding portion 17 and protrudes continuously downward from the center of the bottom of the holding portion 17. The neck portion 18 is guided along a slit 21a between guide rails 21 of the transport unit 20.

The turntable (rotating part) 19 comprises a disk portion 19a and engaging portion 19b. The disk portion 19a is a resin disk that adjoins the bottom of the neck portion 18. The engaging portion 19b protrudes downward from the center of the disk portion 19a. The outer peripheral surface of the disk portion 19a is disposed in contact with that of a roller 33 and configured to rotate following the roller 33 under friction.

The engaging portion 19b projects downward along the axis of rotation and is rotatably engaged with and held by a supporting portion 24 on a chain belt (chain member) 23 of the transport unit 20.

Figure 4:
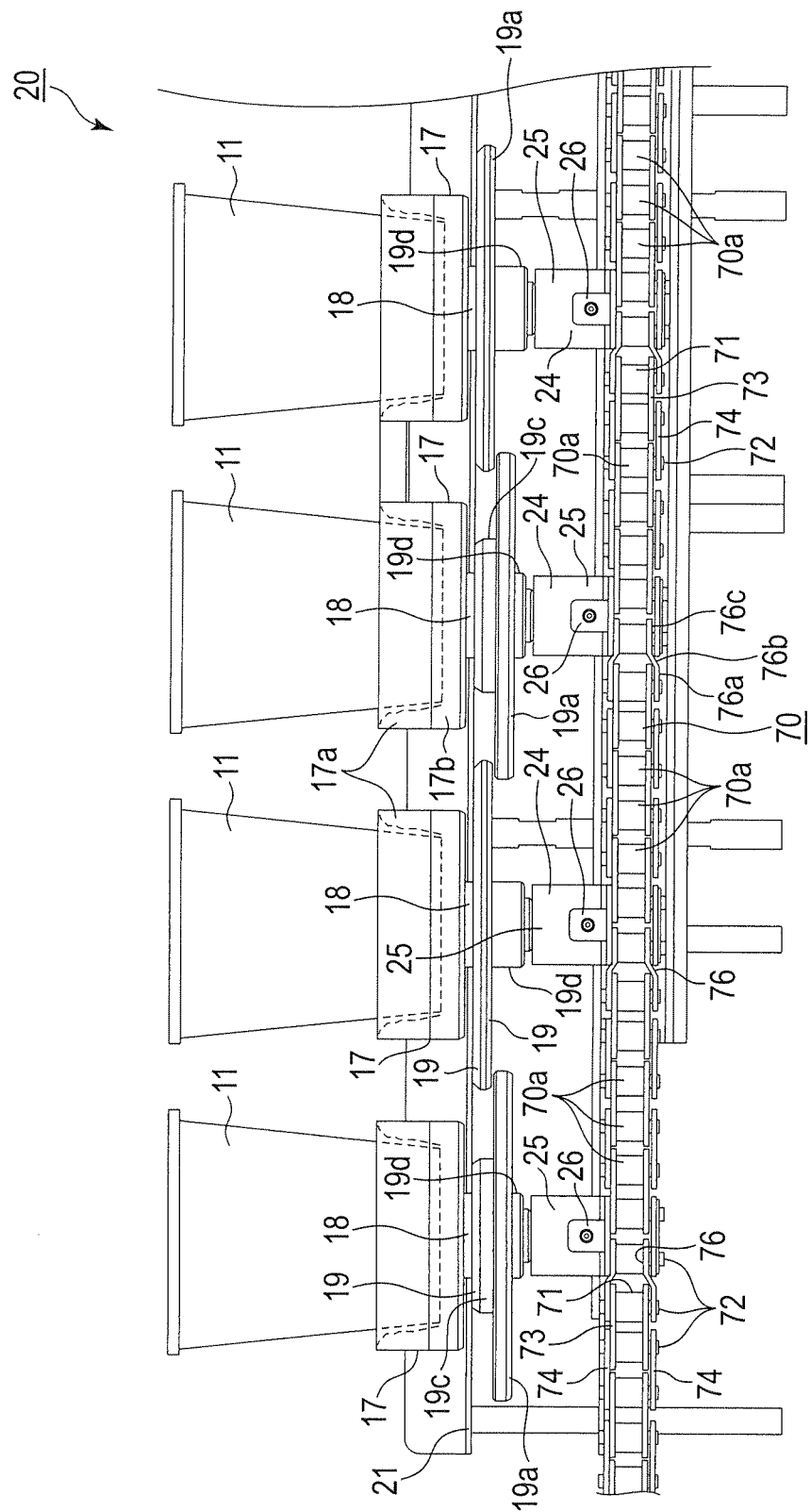
FIG. 4 is a perspective view showing the internal structure of the transport unit according to the embodiment.

As shown in FIG. 4, a circular portion 19d coaxially protrudes from the underside of the disk portion 19a. The circular portion 19d is smaller in diameter than the disk portion 19a and larger than the engaging portion 19b. The pin-like engaging portion 19b protrudes downward from the lower surface of the circular portion 19d. When the engaging portion 19b is fitted into a supporting hole 25a of a block 25, the lower surface of the circular portion 19d contacts the block 25, thereby regulating the height position of the holder 16.

About half of holders 16 that are arranged in a line are each fitted with a regulating plate 19c for regulating the distance between the disk portion 19a and guide rails 21. As the regulating plate 19c is attached to every other holder 16, the positions of the disk portions 19a fixedly arranged side by side on a roller chain 70 are alternately vertically staggered so that the respective outer peripheries of each two adjacent disk portions 19a partially vertically overlap each other. Thus, in each of about half of the juxtaposed holders 16, the guide rails 21 are engaged between the upper surface of the disk portion 19a and the lower surface of the holding portion 17. In each of the other half of the holders 16, the guide rails 21 are engaged between the upper surface of the disk portion 19a and the holding portion 17.

All the holders 16 are arranged so that the distances from the upper end surfaces of their respective neck portions 18 to the lower end surfaces of their respective circular portions 19d are equal.

The transport unit 20 is a chain conveyor system comprising the frame 22, chain belt 23, supporting portion 24, and drive means, such as a transport motor or air actuator, and has the function of transporting the holder 16 along the predetermined transport path. The frame 22 comprises the pair of guide rails 21 extending along the transport path. The chain belt 23 is disposed along the transport path and moves in engagement with the holder 16 below the guide rails 21. The supporting portion 24 supports the holder 16 on the chain belt 23. The drive means serves to feed-drive the chain belt 23.

The slit 21a that defines the transport path is formed between the pair of guide rails 21. Further, one of the guide rails 21 comprises a window portion 21b that is formed by partially cutting off its lateral portion where the roller 33 and turntable 19 face each other. The roller 33 is exposed through the window portion 21b.

Figure 3:
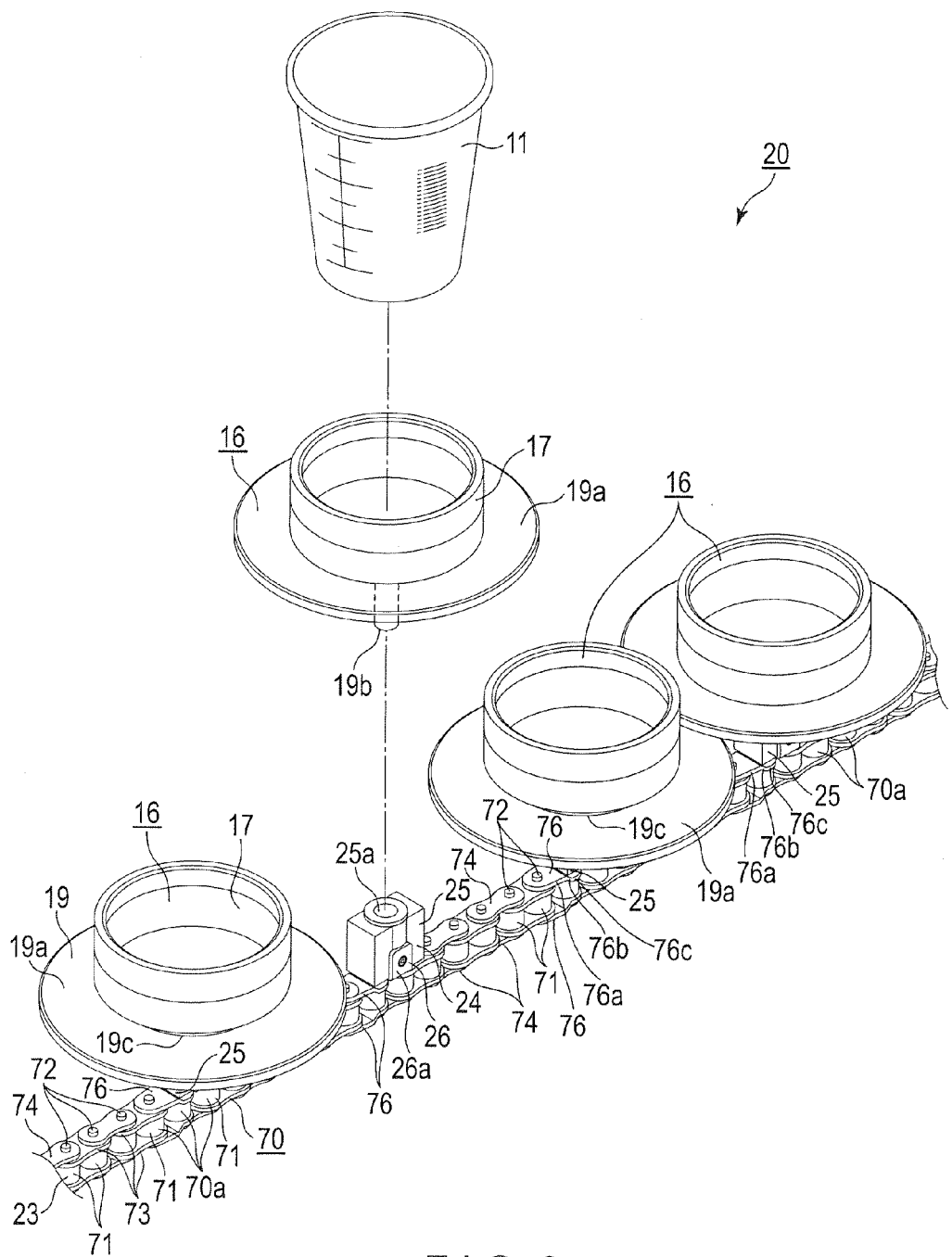
FIG. 3 is a side view showing the internal structure of a transport unit according to the embodiment.

As shown in FIGS. 3 and 4, the chain belt 23 is the roller chain 70 comprising a plurality of link pieces 70a connected to one another. Each link piece 70a comprises a roller 71, shaft 72, a pair of inner plates 73 located at the opposite ends of the roller 71, and a pair of outer plates 74 disposed outside the inner plates 73.

Each of the plates 73 and 74 is a gourd-shaped plate in a plan view and comprises two apertures through which the shafts 72 are passed. A pair of plates 73 and 74 are supported at the opposite ends of each roller 71 by a bushing for pivotal motion about the shaft 72 passed through the roller 71. A plurality of link pieces 70a are pivotably connected to one another in such a manner that each common shaft 72 is passed through and pivotally supported by the respective ones of the apertures of the pair of inner and outer plates 73 and 74 and that another two oppositely adjacent shafts 72 are passed through and pivotally supported by the other apertures.

The roller chain 70 comprises fixing plates 76 arranged at a predetermined pitch. Each fixing plate 76 integrally comprises an outer strip 76a, bent strip 76b, and inner strip 76c, which are continuous with one another. The outer strip 76a is disposed corresponding to the position of the outer plate on each upstream shaft 72. The bent strip 76b is continuously bent inward from the outer strip 76a. The inner strip 76c is disposed corresponding to the position of the inner plate on each subsequent shaft 72. A pair of fixing plates 76 are located at the opposite ends of each shaft 72 in a position where each holder 16 is secured.

The supporting portion 24 is secured to the respective upper surfaces of the downstream inner strip 76c of the fixing plate 76 and the inner plate 73 of the subsequent link piece 70a.

At predetermined positions of the roller chain 70, sprockets for use as power transmission means are provided meshing with the roller chain 70. As the sprockets are rotated by the drive means, that is, the transport motor or air actuator, the roller chain is driven along the transport path. When this is done, the holders 16 supported in predetermined positions on the roller chain 70 move along the transport path.

The supporting portion 24 comprises the block 25 having the supporting hole 25a in which the engaging portion 19b is fitted and supported, and is secured to the respective upper surfaces of the fixing plate 76 and the inner plate 73 located downstream adjacent to it by a bracket 26. The bracket 26 is a bent structure with a U-shaped cross-section and integrally comprises a pair of side strips 26a on either side of the block 25 and a bottom strip connecting the respective lower end edges of the side strips. The bracket 26 holds the block 25 in its top opening and secures it to the roller chain 70 in such a manner that the bottom strip is secured to the respective upper surfaces of the fixing plate 76 and inner plate 73 by screws and that the side strips 26a are secured to the opposite side portions of the block 25.

As shown in FIG. 4, the supporting portions 24 are secured on the chain belt 23 at a predetermined pitch. The pin-like engaging portion 19b projecting downward from each holder 16 is fitted into and held in the supporting hole 25a of the block 25 of each supporting portion 24.

As shown in FIG. 2, the turntable 19 is disposed below the pair of guide rails 21, and the holding portion 17 above the guide rails 21. The holder 16 is anchored to the frame 22 with its neck portion 18 allowed to move guided by the slit 21a between the guide rails 21. Below the turntable 19, moreover, the engaging portion 19b is engaged with and held by the supporting portion 24 on the chain belt 23.

The stirring unit 30 comprises a rotation mechanism section 31 configured to rotate the holder 16 that holds the cup 11, in which the specimen 12 is accommodated, in an upright position. The rotation mechanism section 31 comprises a stirring motor 32 controlled by the control unit 50 and the roller 33 connected to the motor 32 for rotation. In this arrangement, the disk portion 19a of the holder 16 that rotates following the rotation of the roller 33 serves as a part of the power transmission function of the rotation mechanism section 31.

The roller 33 is a circular cylinder of resin. The roller 33 functions as a power transmission system that is rotated by the stirring motor 32 and rotates the disk portion 19a in contact with its outer peripheral surface of resin.

As shown in FIG. 1, a barcode reader 34 is provided beside the stirring unit 30. The barcode reader 34 detects the barcode 11b attached to the side of the cup 11, thereby detecting various displayed data, in the initial stage of rotation of the cup 11 during the stirring operation.

The aliquoting/dispensing unit 40 is located downstream adjacent to the stirring unit 30 in the transport path. The aliquoting/dispensing unit 40 comprises a tilting unit 41, nozzle 42, moving arm 43, and drive unit. The tilting unit 41 tilts the cup 11 after the stirring, for example. The nozzle 42 distributes and dispenses the specimen 12 in the cup 11. The moving arm 43 supports and activates the nozzle 42. The drive unit actuates the moving arm 43 and nozzle 42. The aliquoting/dispensing unit 40 operates at a predetermined timing under the control of the control unit 50.

The tilting unit 41 comprises a pressing piece 41a capable of advancing and retreating. The tilting unit 41 advances or retreats the pressing piece 41a at a predetermined timing under the control of the control unit 50, thereby pressing a predetermined position on the side of the cup 11 to a predetermined angle immediately after the stirring so that the cup 11 is tilted.

The nozzle 42 is configured so that it can suck in and discharge a predetermined amount of the specimen 12 and can move up and down (or advance and retreat). The nozzle 42 is movable as the moving arm 43 is operated under the control of the control unit 50.

The following is a description of the operation of the specimen processing apparatus 10 according to the present embodiment.

The drive means for transport is driven by the control unit 50 to run the chain belt 23 with the holder 16 rotatably supported by the frame 22 in the transport unit 20. As the chain belt 23 is run in this manner, the holder 16 moves in an upright position along the transport path.

For example, the sprockets that mesh with the chain belt 23 are rotated to move the chain belt 23 in a feed direction. As the roller chain 70 thus moves, the holders 16 supported by the blocks 25 secured on the plates 76 and 73 that are arranged at the predetermined pitch on the roller chain 70 are transferred. When this is done, the pivotally supported holders 16 can be prevented from being misaligned, tilting, or toppling down, so that the cups 11 can be sequentially delivered in an upright position at predetermined intervals to processing stations.

The cups 11 are held at the predetermined intervals in the transport path and sequentially flow as the chain belt 23 is run. Thus, the cups 11 can be simultaneously subjected to various steps of processing. Stirring and aliquoting/dispensing processes will now be successively described in connection with one of the cups 11.

When the subject cup 11 reaches the processing station of the stirring unit 30, the control unit 50 suspends the movement of the chain belt 23. Then, the roller 33 is rotated by driving the stirring motor 32. If the roller 33 rotates with its outer peripheral surface 33a in contact with the resin surface of the disk portion 19a of the turntable 19, friction urges the turntable 19 to rotate following the rotation of the roller 33. Thereupon, the holder 16 rotates, and the cup 11 held in the holder 16 rotates in an upright position.

By this rotation, the specimen 12 in the cup 11 is entirely stirred. The rotational speed, time conditions, etc., are determined according to the amount of the specimen 12 and the like, and are set so as to, for example, prevent scattering and achieve a desired stirring accuracy. In the present embodiment, the rotational speed is set to, for example, about 150 to 200 rpm.

In the present embodiment, the barcode reader 34 detects the barcode 11b attached to the side of the cup 11, thereby detecting the various displayed data, while the cup 11 is rotating. Specifically, a reading operation is efficiently performed by detecting the barcode 11b on the side of the stirring cup 11 based on the rotary motion of the cup 11.

After the stirring process, the transport unit 20 is driven to deliver the cup 11 to the aliquoting/dispensing unit 40 on the downstream side. When the subject cup 11 reaches the processing station of the aliquoting/dispensing unit 40, the operation is suspended. Another cup 11 is delivered to the stirring unit 30 and subjected to the same stirring process as described above.

In the aliquoting/dispensing unit 40, the moving arm 43 is driven by the control unit 50 to move the nozzle 42 to the space just above the cup 11.

A tilting operation is performed to tilt the cup 11 such that a predetermined portion of the cup 11 is pressed to a predetermined angle by the tilting unit 41 while the nozzle 42 is moving. If the cup 11 is tilted, the specimen 12 therein collects in the position of the nozzle 42 and its depth becomes so great that it can be easily distributed.

Then, the nozzle 42 is lowered at a predetermined timing and fitted into the tilted cup 11 after the stirring. In this fitted state, a suction operation is performed and a predetermined amount of the specimen 12 in the cup 11 is distributed.

After the distribution, the nozzle 42 is raised to be removed from the cup 11 and is moved to a predetermined dispensing point by the moving arm 43. Then, the specimen 12 is discharged and dispensed into another container, such as a Spitz tube. In this way, the stirring and aliquoting/dispensing processes are completed.

After the end of the stirring process, the pressing piece 41a of the tilting unit 41 is retracted to restore the cup 11 to the upright position, and the transport unit 20 is driven at a predetermined timing to deliver the cup 11 downward. When this is done, another cup 11 having undergone the stirring process on the upstream side is delivered to the aliquoting/dispensing unit 40. A plurality of cups 11 are sequentially processed by repeating these processes.

According to the specimen processing apparatus 10 of the present embodiment, the cups 11 can be moved in an upright position along the complicated transport path. Specifically, each holder 16 is pivotally supported in a predetermined position on the roller chain 70, so that it can be prevented from moving sideways or in the transport direction. Further, torque can be transmitted while maintaining the vertical upright position by means of the holding portion 17 that surrounds and closely holds the lower part of each cup 11.

Since the transport unit 20 has a chain structure, moreover, the holder 16 can be smoothly transported without being misaligned or tilting even in the case where the transport path is a complicated one that is curved and reciprocating. In the case of a belt conveyor in which holders are carried on a belt, a change in transport direction is not easy, and the structure for reciprocating motion is complicated. According to the chain structure of the present embodiment, in contrast, the transport direction can be easily changed, and the reciprocating motion is simple.

In the transport unit 20, moreover, each holder 16 can be attached or detached merely by fitting it into the block 25 from above or removing it upward from the block 25. Thus, the present invention is applicable to a plurality of types of holders, and therefore, to specimen containers of various sizes.

The present invention is not limited directly to the embodiments described herein, and in carrying out the invention, its constituent elements may be embodied in modified forms without departing from the scope or spirit of the invention.

For example, a specimen processing apparatus 100 according to another embodiment shown in FIG. 5 comprises a transport frame 61 in the form of a rectangular plate on its upper surface. A looped transport path A the transport direction of which changes a plurality of times is formed within the plane of the transport frame 61. Various processing stations, such as a stirring unit 30, aliquoting/dispensing unit 40, loading section, unloading section, etc., are provided in predetermined positions along the transport path A.

In this embodiment, a slit 21a extending along the transport path A is formed in the transport frame 61 such that those frame portions on the opposite sides of the slit 21a constitute guide rails 21, individually. A looped roller chain 70 (chain belt 23) comprising a plurality of link pieces 70a connected to one another is disposed along the transport path A below (or behind) the transport frame 61.

As shown in FIG. 5, sprockets 81 that mesh with the roller chain 70 are arranged inside curved portions A1 of the transport path A. Each sprocket 81 comprises a tooth portion on its outer periphery that meshes with the roller chain 70, and its shaft is connected to drive means. In FIG. 5, only two of the sprockets 81 are shown, and illustration of the sprockets 81 at the other curved portions is omitted. Actually, however, the sprockets 81 are disposed individually at all the curved portions, 12 in number, in the transport path A shown in FIG. 5. Sprockets 81 have the functions of positioning the roller chain 70 and transmitting a driving force thereto. The roller chain 70 smoothly runs along the transport path A as any of the sprockets 81 is rotated by the drive means (transport motor or air actuator) with the roller chain 70 meshing with the sprockets 81.

Although a urine sample and cup are given as examples of the specimen and specimen container, respectively, according to the embodiments described herein, the invention is also applicable to other specimens and specimen containers.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen transport and processing apparatus comprising:
   a plurality of holders, each holding a specimen container accommodating a specimen in an upright position;
   a chain member disposed along a predetermined transport path;
   a supporting portion provided in a predetermined position on the chain member and configured to support each holder;
   a guide rail configured to guide each holder along the predetermined transport path, wherein the specimen container is a cylindrical cup which accommodates the specimen, the chain member comprises a plurality of link pieces connected to one another and arranged along the transport path below the guide rail, the chain member comprises the supporting portion comprising a supporting hole, and each holder comprises a holding portion configured to hold an outer peripheral portion of a lower part of the cylindrical cup above the guide rail, a neck portion located below the holding portion and configured to be guided by the guide rail, and an engaging portion located below the neck portion, projecting downward, and configured to be fitted into the supporting hole of the chain member;
   a stirring unit comprising a stirring motor located beside the transport path and a roller attached to an axis of the stirring motor, the stirring unit configured to rotate the specimen container in an upright position by the roller contacting a disk portion provided coaxially with the specimen container, thereby stirring the specimen therein;
   an aliquoting/dispensing unit located downstream relative to the stirring unit in the transport path and configured to distribute and dispense the specimen in the specimen container into another container; and
   a regulating plate located below every other adjacent holder, where the regulating plate vertically spaces the disk portion so that the disk portions are vertically spaced in an alternating fashion.

2. A specimen transport and processing method comprising:
   holding a plurality of specimen containers accommodating a specimen in an upright position, each container held by means of a holder;
   feed-driving a chain member disposed along a predetermined transport path in such a manner that each holder is supported by a supporting portion in a predetermined position on the chain member;
   guiding each holder with a guide rail along the predetermined transport path, wherein the specimen container is a cylindrical cup which accommodates the specimen, the chain member comprises a plurality of link pieces connected to one another and arranged along the transport path below the guide rail, the chain member comprises the supporting portion comprising a supporting hole, and each holder comprises a holding portion configured to hold an outer peripheral portion of a lower part of the cylindrical cup above the guide rail, a neck portion located below the holding portion and configured to be guided by the guide rail, and an engaging portion located below the neck portion, projecting downward, and configured to be fitted into the supporting hole of the chain member;
   rotating the specimen container with a stirring unit comprising a stirring motor located beside the transport path and a roller attached to an axis of the stirring motor, the stirring unit rotating the specimen container in an upright position by the roller contacting a disk portion provided coaxially with the specimen container, thereby stirring the specimen therein;

distributing and dispensing the specimen in the specimen container into another container with an aliquoting/dispensing unit located downstream relative to the stirring unit in the transport path; and vertically spacing in an alternating vertical fashion the disk portions corresponding to every other adjacent holder with a regulating plate which is located below every other adjacent holder.

\* \* \* \* \*